United States Patent [19]
Santhanam

[11] Patent Number: 6,043,300
[45] Date of Patent: Mar. 28, 2000

[54] LIQUID RHEOLOGICAL ADDITIVES FOR NON-AQUEOUS SYSTEMS AND NON-AQUEOUS SYSTEMS CONTAINING SUCH LIQUID RHEOLOGICAL ADDITIVES

[75] Inventor: Mahalingam Santhanam, E. Windsor, N.J.

[73] Assignee: Rheox, Inc., Hightstown, N.J.

[21] Appl. No.: 09/023,064

[22] Filed: Feb. 13, 1998

Related U.S. Application Data

[63] Continuation-in-part of application No. 08/761,870, Dec. 9, 1996, Pat. No. 5,723,653.

[51] Int. Cl.⁷ .............................. C08K 5/10; C08L 63/02
[52] U.S. Cl. ........................... 523/455; 524/196; 524/307
[58] Field of Search ............................ 523/455; 524/196, 524/307

[56] References Cited

U.S. PATENT DOCUMENTS

| | | | |
|---|---|---|---|
| 4,540,734 | 9/1985 | Short et al. .............................. | 524/507 |
| 5,034,444 | 7/1991 | Yun et al. ................................ | 524/223 |
| 5,536,871 | 7/1996 | Santhanam ............................... | 560/196 |

*Primary Examiner*—Robert Dawson
*Assistant Examiner*—D. Aylward
*Attorney, Agent, or Firm*—Michael J. Cronin

[57] ABSTRACT

A liquid, pourable 100% active rheological additive especially useful for thickening non-aqueous compositions is described. The additive, which exists in a pourable form at up to a 100% as a rheologically active composition, exhibits excellent thickening efficiency for systems including inks, epoxies, polyesters, paints, greases and other systems, including ease of dispersibility, without adversely affecting gloss. The additive may operate by both an associative and a reaction mechanism to provide rheological viscosity properties to such systems, and is also similarly useful for aqueous systems.

One important aspect of the present invention relates to a liquid rheological additive composition comprising a reaction product obtained from the reaction of:

a) One or more active hydrogen compounds, wherein the active hydrogen compound contains at least two active hydrogen moieties; and b) One or more compounds containing at least two moieties which are capable of reacting with the active hydrogen moieties of (a), wherein the active hydrogen moieties of compound a) are in stoichiometric excess of the reactive moieties of compound b);

and the reaction product has at least two active hydrogen moieties at its termini.

24 Claims, No Drawings

LIQUID RHEOLOGICAL ADDITIVES FOR NON-AQUEOUS SYSTEMS AND NON-AQUEOUS SYSTEMS CONTAINING SUCH LIQUID RHEOLOGICAL ADDITIVES

This is a continuation-in-part application of U.S. patent application Ser. No. 08/761,870 filed Dec. 19, 1996 allowed Oct. 22, 1997 now U.S. Pat No. 5,723,653.

FIELD OF THE INVENTION

The invention herein is directed to an improved rheological additive for non-aqueous systems which is in a liquid form and is pourable at ambient temperatures. Such an additive imparts improved rheological activity to many types of non-aqueous compositions and systems, including paints, coatings, sealants, inks and varnishes. The present invention is also directed to non-aqueous compositions and systems containing such additives.

BACKGROUND OF THE INVENTION

Rheological additives, generally referred to as thickeners, thixotropes or rheological control agents, have long been used in painting compositions for various purposes. Thus, additives such as viscosity control agents, storage-stability agents, anti-settling agents, sag-control agents, and other materials are added to non-aqueous paint and coating compositions in minor amounts. Rheology additives or modifiers (also often called thickeners, rheological control additives and modification thixotropes) are added to such compositions not only to alter the viscosity of the coating composition, but also to maintain the viscosity at desired levels under varying process conditions and end-use situations. Other effects obtained from rheology modifiers include improvement in pigment suspension, leveling and flow. Some of these properties are also desired in other types of compositions, for instance, oil well drilling fluids. For purpose of this invention, chemical compositions providing one or more of the above properties are referred to as rheological additives, and the properties imparted are all included within the term thixotropy.

Such rheological control agents, to be effective, especially for paints and coatings, must provide proper control characteristics to the systems in which they are employed.

For example, organophilic clays have been shown to be useful to thicken various organic and solvent-based compositions. Among numerous United States patents owned by Rheox, Inc., the assignee of this invention, several describe various kinds of organically - modified clays as rheological additives—see U.S. Pat. Nos. 4,208,218; 4,412,018; 4,517,112; 4,695,402; and 5,075,033. Fumed silica and precipitated silica have also been used to thicken certain types of organic systems.

Organically modified clays and silicaceous materials present drawbacks, however, for thickening non-aqueous compositions. Both organically modified clays and fumed silica exist in solid particulate, or powder form, and these materials generally must be added as solids during the grind stage of manufacture of the compositions to be thickened. Organoclays have sometimes been sold as liquid gels, where the organoclay is dispersed into an organic liquid, in order to avoid the disadvantages of using a solid thickener, but such products have limited acceptance in the marketplace.

The use of these types of additives can also lead to a loss of gloss and quality in the final paint or coating. Furthermore, these additives cause the systems in which they are incorporated to exhibit extremely rapid recovery following shear, thereby limiting the leveling or smoothness of the applied composition.

Some of the problems of use and dispersibility associated with the solid or powder types of such thickeners as organoclays are overcome by the use of polyamide rheological additives. For example, Rheox, Inc. U.S. Pat. No. 4,778,843 describes a solid polyamide rheological additive especially designed for organic solvent-based compositions, which comprises the reaction product of polycarboxylic acid, an active hydrogen compound of a specified carbon chain length and structure, and a monocarboxylic acid capping agent. Recent Rheox U.S. Pat. No. 5,349,011 describes a polyamide-ester rheological additive, especially for organic, solvent-based compositions, which comprises the reaction product of polycarboxylic acid, an active hydrogen composition of a specified structure, an alkoxylated polyol, and a monocarboxylic acid capping agent. Said additive is described as exhibiting excellent efficiency and ease of dispersibility when used in aliphatic solvent-based coating compositions, and as effective when dispersed into a solvent.

U.S. Pat. No. 4,337,184 describes a rheology modifier useful in water-based and organic solvent-based compositions derived from the reaction of polyalkylene oxide, polyfunctional material which includes polyols, amines, amine alcohols, thiols and polyisocyanates, including diisocyanates and water. The modifiers are characterized by having a branched structure and containing substantially no terminal hydrophobic moities.

While not a rheological additive, U.S. Pat. No. 4,072,641 describes polyamide resins useful as flexographic ink vehicles which are prepared by reacting polymeric fatty acids, an alkylene diamine, a mono amino alcohol which is neither branched nor ethoxylated, and a chain-stopping agent, which agent includes a particular branched chain monocarboxylic fatty acid. U.S. Pat. No. 5,100,438 describes an ester-amide additive useful for coal-water slurries which is obtained by the reaction of a polycarboxylic acid with a polyether glycol and an aliphatic amine. Salts of these ester-amides are also disclosed. The resulting materials are combined with water, and the water in turn is mixed with the coal in a mixer. The resulting slurries are liquids at ambient temperature.

Rheox U.S. Pat. No. 4,499,233 describes a water-dispersible modified polyurethane polymer as a viscosity increasing composition for aqueous systems. The polymer is discussed as the reaction product of a polyisocyanate, a polyether polyol in a defined molar range, a modifying agent, and a capping agent reactive with the reactive product of the polyisocyanate, the polyether polyol and the modifying agent. Capping agents described include mercaptans, primary and secondary amines and monoisocyanates.

Recent U.S. Pat. No. 5,319,055 shows a thickening agent for thickening solvent-containing compositions described as the reaction product of a polyol containing at least two hydroxyl groups, a polyisocyanate containing at least two isocyanato - groups and an active hydrogen compound having the formula R-X wherein X is selected from the group consisting of primary amino, secondary amino, and hydroxyl, and R represents a group comprising from 1 to 30 carbon atoms. All the active hydrogen compounds shown in the examples are mono-functional except for examples 5 and 15 which have dual functionality. The thickening agents produced are dispersed into solution with toluene prior to being used as thickeners for non-aqueous dispersions.

Two recent patents issued to Rheox, Inc., describe liquid pourable rheological additives based on two types of alkoxylated nitrogen-containing chemistry—see U.S. Pat. Nos. 5,536,871 and 5,510,452, the teaching of which are incorporated by reference herein.

The aforesaid thickeners are in the main, solid products, unless mixed with solvents.

DISADVANTAGES OF CURRENT SYSTEMS

In the past, commercially available rheological additives for non-aqueous systems based on polyamide and similar chemistries have most often been prepared in solid form, and have been produced and used as thickeners in a dry, solid form. Dispersion in the final formulation is critical for the activation of the additive, and viscosity efficiency is a direct function of successful dispersion into the system to be thickened. However, solid rheological additives have exhibited poor dispersibility when added to organic systems. In addition, dust concerns encountered are similar to those with other types of particulate materials, such as fumed silica. Thus, when added to organic paints, for example, solid additives by their nature tend to agglomerate and form clumps. Such clumping can be reduced by adding the additive to the system with agitation. Dispersion is often very slow, and often adversely impacts the efficiency of specific manufacturing operations.

Particularly in formulations comprising other chemicals and ingredients of the type found in paint systems, extended agitation and aging periods are required before proper incorporation of solid thickeners is attained. Even when such additives are furnished as diluted dispersions they remain difficult to disperse.

Manufacturers have searched for a more effective way of introducing various thickeners into non-aqueous systems. To satisfy this desire, several commercial polyamide-type thickeners and other rheological additives are today sold for paint and other compositions as liquids. However, these commercial thickening compositions are most often made by dissolving or dispersing solid rheological additives into an organic liquid medium or solvent. The choice of the nature and amount of the liquid medium depends on the desired viscosity of the thickening composition mixture. Typically, the viscosity of the pourable thickening composition mixture ought to be less than about 250–300,000 cP (at 10 RPM with a Brookfield RVT viscometer) so that it will readily pour from the storage container as a liquid, and rapidly incorporate into the system to be thickened at room temperature. The solvent selected for such commercial composition has, up to this time, usually been a volatile organic solvent such as toluene, propanol or butyl CARBITOL®. Ranges of ratios of 20% to 50% rheological additive to 50% to 80% solvent are common for such commercial liquid products.

The reduction of release of organic vapors in the use of various types of paints and in the manufacture of inks, polyesters, and coated articles has become important in combating atmospheric pollution. The United States has imposed increasingly stringent limitations upon the emission of such gases to the atmosphere.

The use of volatile organic solvents with rheological additives as described above contributes to the overall volatile organic content ("VOC") of the system that will be thickened. Rheological additives are used at relatively low levels in organic and aqueous systems; however, they may still contribute to the total VOC of the system, because they are typically provided as solutions or dispersions in the aforesaid organic solvent mixtures. This solvent evaporates after products containing such chemicals are applied, and enters the atmosphere during the drying and/or curing of the system. Similar evaporation occurs during the manufacture of inks, sealants, and greases.

A liquid thickening composition having little or no VOC will inherently contribute little or zero VOC to the system being thickened, while having the pronounced advantage of being pourable.

Rheological additives must provide high levels of viscosity or thickness to systems, which prior to such addition are often less viscous. Some systems, such as grease, must become gel-like as a result of the addition. Rheological additives must be efficient, even when added at very small relative weight levels, and must, therefore, have the ability, at such levels, to impart significant increases in viscosity to much larger volumes of organic systems. Rheological additives, in fact, often must impart to systems at very low shear rates a behavior that approaches that of a solid. These requirements led many scientists to conclude that such additives must themselves have very high viscosity levels, and they must be either solid or solid-like. A rheological additive, which could in some circumstances be liquid and pourable, and could at a 100% concentration be less viscous than the system to be thickened (where it would be present at a level of around 0.1% to 3%) appeared, and still appears to some scientists, to be a physical and theoretical impossibility.

Despite the wide variety of rheological additives known in the art, research has been independently and simultaneously conducted toward both active liquid thickeners that are in pourable forms, and which are highly efficient and are readily dispersible in the composition to be thickened; and, in addition, toward non-VOC-containing rheological additives which overcome the deficiencies associated with prior art volatile solvent-mixed thickeners.

The present invention satisfies these twin long-sought goals.

OBJECT AND SUMMARY OF THE INVENTION

OBJECT OF THE INVENTION

It is an object of the present invention to provide a nearly 100% active liquid rheological thixotrope which is either entirely free of volatile solvents, or contains a greatly reduced amount of such solvents, in an easily pourable, pumpable form, and which is fluid at ambient temperatures, for systems including inks, paints, epoxies, polyesters and coatings.

It is a specific object of the present invention to provide said rheological additive in pourable liquid form which is efficient in thickening and providing rheological properties to non- aqueous compositions.

It is a further object to provide a liquid rheological additive made from readily available inexpensive chemical raw materials using relatively simple and easy to use chemical reactions.

It is still further object of the present invention to provide improved organic compositions containing such liquid rheological additives.

SUMMARY OF THE INVENTION

This invention is of a rheological additive, which is pourable at ambient temperatures, and which provides effective and efficient thixotropic properties when used at low levels in nonaqueous systems. Unlike prior additives, this rheological liquid additive is nearly completely rheologically active and efficient, and does not require a diluent to maintain a liquid state. The invention also covers improved organic and solvent systems containing such rheological additives. The term non-aqueous system is used herein to include both solventless and solvent containing compositions.

The advantages of the present invention over the prior art are quite numerous. These new rheological agents may be solvent-free (zero volatile organic compound ("VOC")), and are easily pourable and pumpable liquids at ambient temperatures and easy to handle. They provide high efficiencies at low shear rates, and provide anti-sag properties to fluid coating films. They are readily dispersible in solvent-based systems, requiring no set minimum or maximum temperature for incorporation.

One important aspect of the present invention relates to a liquid rheological additive composition comprising a reaction product obtained from the reaction of:
  a) One or more active hydrogen compounds, wherein the active hydrogen compound contains at least two active hydrogen moieties; and
  b) One or more compounds containing at least two reactive moieties which are capable of reacting with the active hydrogen moieties of (a);
wherein the active hydrogen moieties of compound a) are in stoichiometric excess of the reactive moieties of compound b); and wherein the reaction product has at least two active hydrogen moieties at its termini.

Further advantages and features of the invention, as well as the scope, nature and utilization of the invention, will become apparent to those of ordinary skill in the art from the description of the preferred embodiment of the invention set forth below:

DESCRIPTION OF THE PREFERRED EMBODIMENTS

The liquid additives of this invention may be made using a variety of materials and by a variety of methods either disclosed hereafter, or which will appear obvious when the disclosure of this patent occurs. Applicants do not intend to limit the materials or methods of manufacture of such additives by the following descriptions.

The present invention in one aspect covers a rheological additive composition for non-aqueous system which when substantially free of diluent, is liquid and pourable at ambident temperature and imparts thixotropy to such systems comprising a reaction product obtained from the reaction of:
  a) One or more active hydrogen compounds, wherein the active hydrogen compound contains at least two active hydrogen moieties; and
  b) One or more compounds containing at least two reactive moieties which are capable of reacting with the active hydrogen moieties of (a);
wherein the active hydrogen moieties of compound a) are in stoichiometric excess of the reactive moieties of compound b); and
wherein the reaction product has at least two active hydrogen moieties at its termini.

Active hydrogen compounds preferred for the purposes of this invention are compounds having the formula $(H-X)_m-R-(Y-H)_n$ where X and Y are independently selected from the group comprising heteroatoms, m and n are $\geq 1$ and R represents a group containing 2 to 100 carbon atoms and may contain other functionalities which are unreactive to the component b); the preferred heteroatoms being oxygen and nitrogen.

Compounds useful for element a) can be selected from polyols, amino alcohols and diamines.

Useful polyols include any aromatic, aliphatic or cycloaliphatic, straight chain or branched chain, saturated or unsaturated polyol which has at least 2 carbon atoms, and more preferably 2 to 40 carbon atoms. Examples of these include 1,2 ethanediol, 1,2- and 1,3-propanediol, 1,4- and 1,3-butanediol, 1,5-pentanediol, 1,6-hexanediol, 2,5-hexanediol and the like either alone or in mixtures thereof. Included in useful polyols are dimer diols. Dimer diols are commercially available under the trade name Empol from Henkel Corporation—Emery Group. Illustrative example of a dimer diol is Empol 1075.

Also included in the polyols useful in this invention are polyether polyols which may be a homopolymer, or a block or random copolymer having the repeating unit:

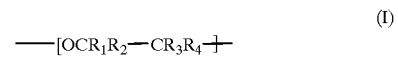

wherein $R_1$, $R_2$, $R_3$ and $R_4$ of each oxyalkylene unit are independently selected from the group consisting of H, $CH_3$ and $C_2H_5$. These polyether polyols have a hydroxy functionality at each termini of polyether chain. Exemplary examples of such polyether polyols are polyethylene glycols, polypropylene glycols, poly(ethylene-propylene) glycols and polytetrahydrofurans.

Primary diamines such as $\alpha,\omega$-Diamino polyethers, for example Jeffamine D-400, represent another important class of preferred active hydrogen compounds useful in the practice of this invention.

Compounds particularly preferred for element a) include alkoxylated aliphatic amine diols and alkoxylated aliphatic amide diols which are liquids at ambient temperatures. These compounds can normally be selected from tertiary amines with one alkyl group and preferably two hydroxyalkyl or polyoxyalkylene groups attached to the nitrogen atom and have a general chemical structure represented by the following formula:

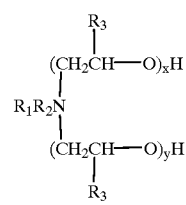

wherein:
(1) $R_1$ is a pendent straight or branched chain alkyl, saturated or unsaturated, radical having 6 to 40 carbon atoms, preferably 8 to 20 carbon atoms, and most preferably 10 to 18 carbon atoms. Especially preferred is where $R_1$ is a fatty alkyl having 11 to 17 carbon atoms such as coco, stearyl, soya, tallow, hydrogenated tallow, oleyl and mixtures thereof.
(2) $R_2$ is

or $-CH_2-$ and
3) $R_3$ is hydrogen or methyl.

The oxyalkylene group when employed is represented by the formula:

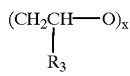

wherein $R_3$ is a hydrogen or methyl group and x is 1 or 2 and is preferably ethoxyl, propoxy or a mixture thereof. At least one of x or y is at least 1 preferably both x and y are at least 1 and the sum of x+y is from 1 to 40, preferably 2 to 30, and most preferably 2 to 20.

Illustrative examples of alkoxylated aliphatic amine diols useful in this invention, represented by formula (II), are available under the trade name Varonic from Witco Corporation and Ethomeen from Akzo Chemie America.

Lower molecular weight compounds which are liquid at ambient temperatures are particularly useful.

Amino alcohols useful as element (a) of this invention should contain one primary or secondary amino group and one or more hydroxy groups. Illustrative examples of useful amino alcohols are monoethanolamine, 2-amino-2-methyl-1-propanol, 3-amino-1-propanol, 2-(2-aminoethoxy)ethanol and mixtures thereof. Higher functionality active hydrogen containing compounds with 3 or more active hydrogen groups may be used as a portion of the total diols; however, their use might be limited in some circumstances since such use might lead to the formation of crosslinked gels which are unsuitable in the environment of the organic formulation in which the invention is to be used.

Although in some cases solids such as 1,6-hexanediol have proved effective, it is most preferred that compound a) be a compound which is a liquid at ambient temperature and of lower molecular weight in order to maximize the likelihood that a liquid reaction product be obtained.

Compounds useful for element b) can be any compound containing at least two moieties which are capable of reacting with the active hydrogen moieties of compound a). Preferably, the active functional moiety is selected from compounds containing carbonyl groups. These compounds are selected from either polycarboxylic acids or polyisocyanates and mixtures thereof with polycarboxylic acids being preferred.

Polycarboxylic acids useful for this invention should be selected from aromatic, aliphatic or cycloaliphatic straight chain or branched chain, saturated or unsaturated dicarboxylic acids which have at least 2 carbon atoms, and more preferably 3 to 40 carbon atoms. Examples of useful products are adipic acid, oxalic acid, malonic acid, succinic acid, glutaric acid, pelargonic acid, suberic acid, azelaic acid, undecanedioic acid, 1,11-undecanedicarboxylic acid, dodecanedioic acid, hexadecanedioic acid, docosanedioic acid, maleic acid, fumaric acid and the like with adipic acid being a preferred acid. Likewise, polymeric polyacids, such as polybutadiene dicarboxylic acids, can be employed. The term polycarboxylic acid includes hydroxy substituted dicarboxylic acids and oxadicarboxylic acids. Representative of hydroxy substituted dicarboxylic acids are tartaric acid, citric acid and hydroxyisophthalic acid. Representative of useful oxadicarboxylic acids are 3,6,9-trioxaundecanedioic acid and polyglycol diacid.

Dicarboxylic acids of oligomers of fatty acids having carbon chain of from 16 to 20 carbon atoms are preferred as compound b). Exemplary fatty acids are those derived from soybean oil, tall oil, corn oil, linseed oil, cottonseed oil, castor oil, kapok seed oil, rice bran oil and mixtures thereof.

Even further preferred are oligomers of fatty acids which are substantially comprised of dimerized fatty acid-such are often called "dimer acids." These dimerized fatty acids constitute at least 75% by weight of dibasic acid. The oligomerized fatty acid preferably also has a low monomer content such as less than about 8% by weight. The dimerized fatty acids also has a low polybasic acid content such as less than about 20% by weight. Useful dimer acids are commercially available under the trade name Empol Dimer Acids from Emery Industries, and Pripol Dimer Acids from Unichema, International. Illustrative commercial examples of useful dimer acids are Empol 1004, Empol 1008, Empol 1018, Empol 1016 and the like. Mixtures of polycarboxylic acids can also be employed.

In addition to the dicarboxylic acids, polybasic acids which contain more than two carboxylic acid groups are also useful. Representative example of these polybasic acids are trimellitic acid, trimesic acid, citric acid, 1,2,3,4-butane tetracarboxylic acid and the like. Polymerized polybasic acids which contain more than two carboxylic acid groups are also included in the definition of polybasic acids. Especially preferred polymerized polybasic acids are fatty acids having carbon chains from 48 to 60. The polymeric polybasic acids with 3 carboxylic acid groups are known as "trimer acids". These trimer acids are commercially available under the trade name Empol from Henkel Corporation—Emery Group and Unidyne from Union Camp Corporation. Representative examples of these trimer acids are Empol 1040, Empol 1041, Empol 1052, and Unidyme 60. A most preferred trimer acid is Empol 1040. Empol 1040 is substantially comprised of by weight of polybasic acid (67%), dibasic acid (31%), and monobasic acid (2%). The amount of acid selected for use can be important. If the amount selected is excessive then a highly elastic and insoluble material may result.

Polyisocyanates which can be employed in this invention contain at least two isocyanate groups per molecule and can be linear or branched aliphatic, aromatic or cycloaliphatic. Such polyisocyanates may also be in the form of a prepolymer having two or more unreacted isocyanate moieties and having an average molecular weight in the range of from about 500 to about 2,000. The polyisocyanate preferably contains two isocyanate moieties per molecule. Higher functionality polyisocyanates may be used as a portion of the total isocyanate requirement. However, the use of higher functionality polyisocyanates is limited by the possibility of the formation of a crosslinked, insoluble gel which is unsuitable for purposes of the present invention.

Exemplary polyisocyanates useful in the preparation of the compositions of the present invention are 1,4-tetramethylene diisocyanate, 1,6-hexamethylene diisocyanate, 2,2,4-trimethyl-1,6-diisocyanatohexane, 1,10-decamethylene diisocyanate, 1,4-cyclohexane diisocyanate, 4,4"-methylenebis(isocyanatocyclohexane), 1-isocyanato-3-isocyanatomethyl- 3,5,5-trimethylcyclohexane, m- and p-phenylene diisocyanate, 2,6- and 2,4-tolylene diisocyanate, xylylene diisocyanate, 4-chloro-1,3-phenylene diisocyanate, 4,4"-biphenylene diisocyanate, 4,4"-methylene diphenylisocyanate, 1,5-naphthalene diisocyanate, 1,5"-tetrahydronaphthalene diisocyanate, and $C_{36}$ dimer acid diisocyanate, based on dimer acids, sold under the trade name "DDI 1410" by Henkel Corporation. Preferred polyisocyanates are 1,6-hexane diisocyanate and $C_{36}$ dimer diisocyanate.

It should be understood that a variety of additional reactants can be used to prepare the polymers of this invention including chain-extending and modifying agents including diamines, most particularly α,ω diamines, as long as the final reaction product is a liquid.

The inventive rheological compounds according to this invention are formed from the reaction of a) and b). The amount of compound a) may vary from about 15 to 95 parts by weight; amounts of compound b) may vary from about 5 to 85 parts by weight. It is critical to this invention that the active hydrogen moieties of compound a) be in stoichiometric excess of the reactive moieties of compound b) in an amount so that no substantial unreacted compound a) remains after the reaction is completed.

The product of this reaction preferably is a polymer with a molecular weight of <50,000 which is a liquid. High molecular weight products often produce solid materials. Such solids can function as rheological additives, but are not suitable for purposes of the present invention. The rheological additives of the present invention are fully liquid and of a molecular weight that permits pourability.

The order of the addition of the co-reactants is not generally important. Generally compounds a) and b) are added together. The active hydrogen moieties of compound a) must be in stoichiometric excess of the reactive moieties of compound b). In the reaction of an active hydrogen compound with a dimer acid and a trimer acid, for example, the reactants can be added all at once and reacted.

Another method of preparation is reacting first compound a) with a dibasic acid with a stoichiometric excess of active hydrogen moieties of a) followed by the addition of a trimer acid, for example, to form the reaction product of this invention.

Polymers are most usefully defined as reaction products because they are in fact mixtures of a wide variety of statistical permutation compounds of varying molecular length and weight. Without intending to change the above, what follows are idealized representations of chemical formula of the reaction product of this invention. The purpose of the below is to show the principle of the instant invention of providing a polymer reaction product that retains reactive moieties on its termini—note the active hydrogen group on the right end of each long chain.

The products of this invention made with a trimer acid may be represented by the general idealized formula:

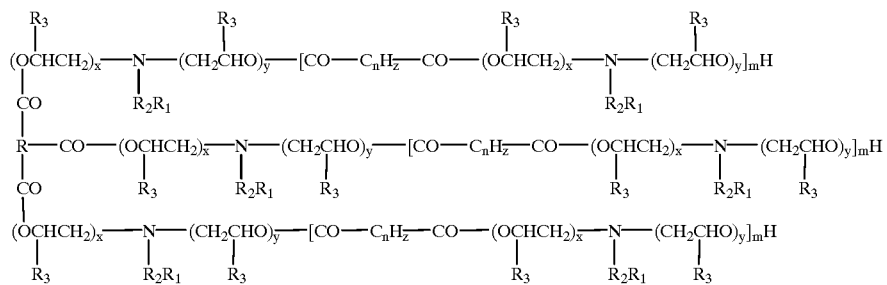

where R is a fatty straight or branched alkyl, saturated or unsaturated, radical having 45 to 60 carbon atoms, $R_1$ is a fatty straight or branched alkyl, saturated or unsaturated, radical having 6 to 40 carbon atoms, $R_2$ is >C=O or —$CH_2$—, $R_3$ is hydrogen or methyl, each n is from 30 to 40, each z is approximately 60 to 80, each x+y is from 1 to 40, and each m is from 1 to 100 inclusive.

A convenient method for preparing the reaction product of the invention is follows: A typical ratio of the reactants is about 3 moles of compound (a) and 2 moles of compound (b) heated to eliminate water. In the reaction of 3 moles of alkoxylated amine diols with 2 moles of dimerized fatty acid, reacted to a temperature of 200° C., the reaction product formed is represented by the general idealized formula:

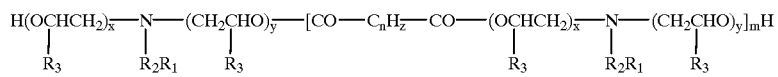

where $R_1$ is a fatty straight or branched alkyl, saturated or unsaturated, radical having 6 to 40 carbon atoms, $R_2$ is >C=O, or —$CH_2$—, $R_3$ is hydrogen or methyl, n is from 30 to 40, z is approximately 60 to 80, each x+y is from 1 to 40, and the average of m is 2.

About 3 moles of the above product can be further reacted with about one mole of trimerized fatty acid through a condensation reaction, by heating to eliminate water to form the reaction product represented by the general idealized formula—here again note that each linear chain is terminated by an active hydrogen group:

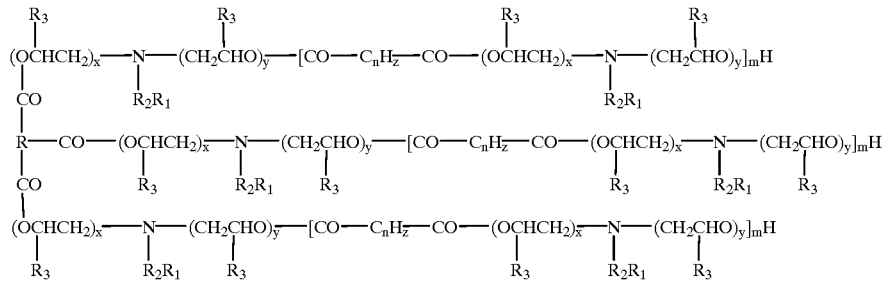

where R is a fatty straight or branched alkyl, saturated or unsaturated, radical having 45 to 60 carbon atoms, $R_1$ is a fatty straight or branched alkyl, saturated or unsaturated, radical having 6 to 40 carbon atoms, $R_2$ is $>C=O$ or $—CH_2—$, $R_3$ is hydrogen or methyl, each n is from 30 to 40, each z is approximately 60 to 80, each x+y is from 1 to 40, and the average of each m is 2.

It should be noted that some cross-linking may occur, either in the first stage or in the second stage, particularly in the reaction with a trifunctional reactant, such as a trimer acid. Some cross-linking is unavoidable, and is not objectionable so long as the final product is liquid at ambient temperature and may in some cases be of some advantage. But excessive cross-linking is undesirable, resulting in insoluble, difficult to handle gels which may be unsuitable for the purposes of the present invention.

The reactants may be charged in increments to a suitable reaction vessel equipped with a mechanical stirrer, a thermometer, a Dean-Stark adapter or other water collector and a nitrogen inlet. The reactants can be heated under a blanket of nitrogen. The reaction may be carried out under atmospheric pressure or under vacuum.

The reaction temperature to be used in the synthesis depends upon the reactants. Thus, the reaction temperature to be used in the reaction of an active hydrogen compound with a polycarboxylic acid preferably ranges from ambient temperature to about 300° C. More preferably, the temperature ranges from ambient to 250° C., and most preferably from 120° C. to 220° C. Water formed during this reaction is removed as condensate as the reaction progresses. After the completion of the reaction, the additive is cooled and discharged. The reaction temperature to be used in the reaction of an active hydrogen compound and an isocyanate preferably ranges from ambient temperature to 150° C. More preferably, the temperature ranges from ambient to 110° C. and most preferably from 60° C. to 100° C. After the completion of the reaction, the solvent, if employed, is removed by a rotary evaporator or the solvent was evaporated off at 80° C. in a vacuum oven overnight.

The additives of the present invention may be synthesized with or without a catalyst. The catalyst, if used, may be selected from those which are normally used for condensation reactions. Examples of such catalysts include but not limited to sulfuric acid, p-toluene sulfonic acid, dibutyltin dilaurate, tetraalkyltin or titanium compounds, metal hydrides and the like. Most preferred catalyst for the reaction of active hydrogen containing compound and dibasic acids is p-toluene sulfonic acid and for the reaction of active hydrogen containing compound and isocyanates is dibutyltin dilaurate and the catalyst should generally be used in an amount of from about 0.001 to 2.5 percent by weight based on the total weight of the reactants.

The additives of the present invention may be manufactured with or without an organic solvent. Since the form of the rheological control agent is a solvent-free pourable liquid, it is preferable to synthesize the product in a solvent free environment. Since the solvent free product may be a viscous and pourable liquid, it may be appropriate to use a solvent at the let down stage during the synthesis to make the product even more pourable. When a solvent is used during synthesis, the type of solvent is not critical except that it should not be reactive with the components of the thickener of this invention. If it is appropriate to use a solvent during the synthesis, the same solvent used in the coating composition in which the rheological additive could be incorporated may be preferred. Preferred solvents, if used at all, for synthesizing the rheological additives of this invention are ketones such as methyl ethyl ketone, methyl isobutyl ketone, esters such as propylene glycol mono methyl ether acetate, aromatic solvents, such as toluene, xylene, aromatic petroleum distillates and mixtures thereof, aliphatic solvents such as hexane, heptane, cyclohexane and aliphatic petroleum distillates and mixtures thereof. The most preferred solvents are aromatic petroleum distillates such as being sold under the trade name Aromatic 100 by Exxon Chemical Company. A combination of solvents could be employed as long as the solvents are compatible. The solvent should generally be used from 0 to 25 percent by weight of the reaction mixture.

The compositions of the present invention are rheological liquids without diluent which effectively impart thixotropic properties to systems in which they are utilized. These properties are at least equal to previously known solid thixotropes. When used, the additives may contain no solvent, or may optionally contain substantially reduced solvent. Organic or other solvent can be used at less than about 10 to 25% by weight, if convenient for either manufacture or use. The rheological additives of the present invention are a substantial improvement over known additives. In contrast to some particulate-type rheological additives, the rheological additives of the present invention have excellent flow and leveling properties, as well as excellent efficiency and easy dispersion characteristics. Compared to recent solid rheological additives disclosed in the art, the rheological additives of this invention can be incorporated in the system as rheological liquids.

While not bound by any theory, the liquid rheological additives of the present invention are believed to function in part as thickeners by interaction with themselves and with components such as resin and pigment in the system to be thickened. The formation of hydrogen bonding due to the active hydrogen groups in the structure of the additives likely influences the makeup of a random network, thereby increasing interaction among the polymers with the resin and the pigment in the composition to be thickened. Such a thickening mechanism may explain why a pourable liquid can at low levels of use provide substantial viscosity to a much larger volume system.

Also the proposed mechanism of associative thickening of systems and solutions is in part through physical interactions between the pendant moieties often associated with compound a) in the thickener molecule. Their associations with one another may create a three dimensional network of thickener molecules that results in a very high viscosity when dispersed into a system. When added to an organic system, the combination of mechanisms in combination with the interactivity of the chain end group allow the thickener to have less association with itself; the thickener molecule then both (i) interacts with and (ii) associates with the organic composition and with itself, and is thereby believed to thicken in a novel and unusual manner. The rheological additives prior to dispersion is fully liquid of a viscosity that permits pourability.

The liquid rheological additive of the present invention may be used to thicken a variety of organic and solvent-based compositions, and the rheological additive may also be used in solvent-free compositions. Non-aqueous solvents including non-aqueous polymer solutions such as, for example, a solution of an alkyd in mineral spirits, dispersions of polymers in non-aqueous media (called non-aqueous dispersions), and non-aqueous paints, paint strippers, adhesives, inks, sealants, mastics, caulks, pigment dispersions, and pigment printing pastes can be advantageously bodied, viscosified, or thickened, by this invention. The additive is particularly useful, for example, in thickening aliphatic and aromatic solvent-based compositions, and may also be used in polar (ketones, alcohols, esters) based compositions. Illustrative organic compositions include aliphatic alkyd paints such as "trade sales" paints, varnishes, epoxy-based paint, polyesters, modified alkyd based paints and alkyd, polyester and acrylic bake enamels, such as standard quality industrial paints, certain sealants and unsaturated polyester resin formulations. The additives are useful in aromatic high solids bake enamels which include systems based on alkyd/melamine, acrylic/melamine, and polyester/melamine system including appliance enamels, and equipment enamels. Additionally, the additives find use in high solids air-dry enamels based on alkyd and modified alkyd formulations.

In addition to aliphatic and aromatic solvent-based systems, the additives of the present invention may also be used in petroleum-based and vegetable oil-based systems. Representative examples of petroleum solvents include Magiesol 52 sold by Magie Bros., Sunprint HP 750 marketed by Sun Inc., and Exprint 705 sold by Exxon Chemical Company. Illustrative vegetable oils include but are not limited to soybean oil, rapeseed oil, canola oil, palm oil, rice bran oil and the like. The additive of this invention can easily be dispersed into the organic composition to provide improved viscosity characteristics. The additive can be dispersed in the composition at any temperature normally used in their production.

Since the additive is an easily pourable or pumpable rheological liquid, it can be incorporated very easily into a variety of compositions at various stages of their preparation. The compositions of this invention can also be added at any stage of the formulation process. They can be added at the beginning of processing, during processing, or as a post-add ingredient.

The amount of rheological additive used in a specific instance is determined by numerous factors, including the type of the organic solvent-based composition to be thickened, and the level of thickening desired. However, a general range is from about 1.5 to about 30 pounds per hundred gallons of formulation. On a weight basis, the amount of the rheological additive is generally from about 0.1 to about 10% by weight, preferably from about 0.1 to about 8% by weight, more preferably from about 0.1 to about 5% by weight and most preferably from about 0.2% to about 3% by weight of the system to be thickened.

The rheological additives of the present invention can provide important advantages in a variety of organic coating compositions. Since the rheological additives of the present invention are solvent-free (zero VOC) or contain substantially reduced solvent (low VOC) they are thus compatible with coating, ink, or polyester systems regardless of VOC specification. Since the rheological additives of the present invention are compatible with the systems to be thickened, they are highly dispersible at low activation temperatures in almost all systems. Furthermore, because the rheological additives impart effective rheological properties to compositions, their use enables coating formulations to be prepared which do not unduly sag or flow when applied to vertical surfaces. As added benefits, the rheological additives of the present invention generally do not show any yellowing of the coating composition and above all do not significantly affect the gloss or fineness of grind of the original paint or coating composition.

The present invention is exemplified and compared in the following examples. However, the Examples should not be construed as limiting the invention.

In the following examples, Ethomeen C-15 is a polyoxyethylene (5) cocoamine (CTFA adopted name-PEG-5 cocoamine), Empol 1004 is a hydrogenated dimer acid produced by the dimerization of $C_{18}$ fatty acids, Empol 1040 is a trimer acid produced by the polymerization of $C_{18}$ fatty acids, DDI 1410 is a dimer acid diisocyanate, based on a long chain dimerized fatty acid backbone.

EXAMPLE 1

This procedure illustrates a two step reaction.

To a 250-ml 4-necked round bottomed flask equipped with a thermometer, a Dean-Stark adapter, a water-cooled condenser, a mechanical stirrer and a nitrogen inlet, 50.64 grams (0.12 mole) Ethomeen C-15 and 45.36 grams (0.08 mole) Empol 1004 were charged. The mixture was heated to 200° C. with stirring under a blanket of nitrogen. Water starts to come off at 170° C. After an hour at 200° C., aliquots are taken hourly and the acid and the amine values are determined. When the acid and amine values are less than 8 and 70 respectively and constant, 11.28 gram (0.013 mole) Empol 1040 were charged and the reaction continued until the acid value is below 8 and the amine value is below 70 respectively. At the end of the reaction, the product was discharged. The product was cooled to ambient temperatures and was a liquid.

EXAMPLE 2

This procedure illustrates the use of a one step reaction.

To a 250-ml 4-necked round bottomed flask equipped with a thermometer, a Dean-Stark adapter, a water-cooled condenser, a mechanical stirrer and a nitrogen inlet, 50.64 grams (0.12 mole) Ethomeen C-15, 45.36 grams (0.08 mole) Empol 1004 and 11.28 grams (0.013 mole) Empol 1040 were charged. The mixture was heated to 200° C. with stirring under a blanket of nitrogen. Water starts to come off at 170° C. After an hour at 200° C., aliquots are taken hourly and the acid and the amine values are determined. At the end of the reaction when the acid value is below 8 and amine value is below 70 respectively, the product was discharged. The product was cooled to ambient temperatures and was a liquid.

EXAMPLE 3

To a 250-ml 4-necked round bottomed flask equipped with a thermometer, a Dean-Stark adapter, a water-cooled condenser, a mechanical stirrer and a nitrogen inlet, 63.3 grams (0.15 mole) Ethomeen C-15 and 56.7 grams (0.10 mole) Empol 1004 were charged. The mixture was heated to 200° C. with stirring under a blanket of nitrogen. Water starts to come off at 170° C. After an hour at 200° C., aliquots are taken hourly and the acid and the amine values are determined. When the acid and amine values are less than 8 and 70 respectively and constant, the product was discharged. The product was cooled to ambient temperatures and was a liquid.

EXAMPLE 4

To a 250-ml 4-necked round bottomed flask equipped with a thermometer, a Dean-Stark adapter, a water-cooled condenser, a mechanical stirrer and a nitrogen inlet, 52.75 grams (0.125 mole) Ethomeen C-15, 56.70 grams (0.10 mole) Empol 1004 and 7.20 grams (0.0083 mole) Empol 1040 were charged. The mixture was heated to 200° C. with stirring under a blanket of nitrogen. Water starts to come off at 170° C. After an hour at 200° C., aliquots are taken hourly and the acid and the amine values are determined. At the end of the reaction when the acid value is below 8 and amine value is below 70 respectively, the product was discharged. The product was cooled to ambient temperatures and was a liquid.

EXAMPLE 5

To a 250-ml 4-necked round bottomed flask equipped with a thermometer, a Dean-Stark adapter, a water-cooled condenser, a mechanical stirrer and a nitrogen inlet, 52.75 grams (0.125 mole) Ethomeen C-15 and 56.7 grams (0.10 mole) Empol 1004 were charged. The mixture was heated to 200° C. with stirring under a blanket of nitrogen. Water starts to come off at 170°C. After an hour at 200° C., aliquots are taken hourly and the acid and the amine values are determined. When the acid and amine values are less than 8 and 70 respectively and constant, 7.20 gram (0.0083 mole) Empol 1040 were charged and the reaction continued until the acid value is below 8 and the amine value is below 70 respectively. At the end of the reaction, the product was discharged. The product was cooled to ambient temperatures and was a liquid.

EXAMPLE 6

To a 250-ml 4-necked round bottomed flask equipped with a thermometer, a Dean-Stark adapter, a water-cooled condenser, a mechanical stirrer and a nitrogen inlet, 50.64 grams (0.12 mole) Ethomeen C-15 and 56.7 grams (0.10 mole) Empol 1004 were charged. The mixture was heated to 200° C. with stirring under a blanket of nitrogen. Water starts to come off at 170° C. After an hour at 200° C., aliquots are taken hourly and the acid and the amine values are determined. When the acid and amine values are less than 8 and 70 respectively and constant, the product was discharged. The product was cooled to ambient temperatures and was a liquid.

EXAMPLE 7

To a 250-ml 4-necked round bottomed flask equipped with a thermometer, a Dean-Stark adapter, a water-cooled condenser, a mechanical stirrer and a nitrogen inlet, 50.64 grams (0.12 mole) Ethomeen C-15 and 59.54 grams (0.105 mole) Empol 1004 were charged. The mixture was heated to 200° C. with stirring under a blanket of nitrogen. Water starts to come off at 170° C. After an hour at 200° C., aliquots are taken hourly and the acid and the amine values are determined. When the acid and amine values are less than 8 and 70 respectively and constant, the product was discharged. The product was cooled to ambient temperatures and was a liquid.

EXAMPLE 8

To a 250-ml 4-necked round bottomed flask equipped with a thermometer, a Dean-Stark adapter, a water-cooled condenser, a mechanical stirrer and a nitrogen inlet, 51.19 grams (0.1213 mole) Ethomeen C-15, 0.64 grams (0.0038 mole) isophorone diamine and 56.70 grams (010 mole) Empol 1004 were charged. The mixture was heated to 200° C. with stirring under a blanket of nitrogen. Water starts to come off at 170° C. After an hour at 200° C., aliquots are taken hourly and the acid and the amine values are determined. When the acid and amine values are less than 8 and 70 respectively and constant, 7.20 gram (0.0083 mole) Empol 1040 were charged and the reaction continued until the acid value is below 8 and the amine value is below 70 respectively. At the end of the reaction, the product was discharged. The product was cooled to ambient temperatures and was a liquid.

EXAMPLE 9

To a 250-ml 4-necked round bottomed flask equipped with a thermometer, a Dean-Stark adapter, a water-cooled condenser, a mechanical stirrer and a nitrogen inlet, 42.20 grams (0.10 mole) Ethomeen C-15, 3.35 gram (0.02 mole) isophorone diamine and 45.36 grams (0.08 mole) Empol 1004 were charged. The mixture was heated to 200° C. with stirring under a blanket of nitrogen. Water starts to come off at 170° C. After an hour at 200° C., aliquots are taken hourly and the acid and the amine values are determined. When the acid and amine values are less than 8 and 70 respectively and constant, 11.54 gram (0.0133 mole) Empol 1040 were charged and the reaction continued until the acid value is below 8 and the amine value is below 70 respectively. At the end of the reaction, the product was discharged. The product was cooled to ambient temperatures and was a liquid.

EXAMPLE 10

A 250 three-necked round bottom flask equipped with a mechanical stirrer, a thermometer, a water-cooled condenser, and a nitrogen gas inlet is charged with 37.98 grams (0.09 mole) Ethomeen C-15 and 140 mL methylisobutyl ketone. The reaction mixture was stirred under a nitrogen blanket. Ethomeen C-15 in methylisobutyl ketone was then heated to 120° C. to azeotropically distill any water which was present in the solution. The solution was cooled to 60° C. and 36.00 grams (0.06 mole) DDI 1410 and 0.001 grams dibutyltin dilaurate were charged to the reaction vessel. The reaction mixture is maintained at 90° C. for two to three hours. The product was cooled to 50° C. and the solvent was evaporated off at 80° C. in a vacuum oven overnight. The product was a liquid. The general procedure outlined in Example 10 was used, except that the reactants were replaced as indicated in Table 1. All examples were viscous pourable liquids at ambient temperatures.

TABLE 1

| Example | Reagents | moles | wt in grams |
| --- | --- | --- | --- |
| 11 | Ethomeen C-15 | 0.16 | 67.52 |
|  | 1,6-Hexamethylene diisocyanate | 0.12 | 20.18 |
| 12 | Ethomeen C-15 | 0.1 | 42.2 |
|  | DDI 1410 | 0.075 | 45 |
| 13 | Ethomeen C-15 | 0.15 | 63.3 |
|  | 1,6-Hexamethylene diisocyanate | 0.12 | 20.18 |
| 14 | Ethomeen C-15 | 0.15 | 63.3 |
|  | 1,6-Hexamethylene diisocyanate | 0.125 | 21.03 |
| 15 | Ethomeen C-15 | 0.16 | 67.52 |
|  | 1,6-Hexamethylene diisocyanate | 0.116 | 19.51 |
|  | DDI 1410 | 0.004 | 2.4 |
| 16 | Ethomeen C-15 | 0.15 | 63.3 |
|  | Isophorone diisocyanate | 0.1 | 22.23 |
| 17 | Ethomeen C-15 | 0.12 | 50.64 |
|  | Isophorone diisocyanate | 0.1 | 22.32 |
| 18 | Ethomeen C-15 | 0.16 | 67.52 |
|  | 1,6-Hexamethylene diisocyanate | 0.112 | 18.84 |
|  | DDI 1410 | 0.008 | 4.8 |

EXAMPLE 19

A 250 mL three-necked round bottom flask equipped with a mechanical stirrer, a thermometer, a water-cooled condenser, and a nitrogen gas inlet is charged with 67.52 grams (0.16 mole) Ethomeen C-15 and 140 mL methylethyl ketone. The reaction mixture was stirred under a nitrogen blanket. Ethomeen C-15 in methylethyl ketone was then heated to 85° C. to azeotropically distill any water which was present in the solution. The solution was cooled to 50° C. and 19.51 grams (0.116 mole) 1,6-hexamethylene diisocyanate and 2.4 grams (0.004 mole) DDI 1410 and 0.001 gram dibutyltin dilaurate were charged to the reaction vessel. The reaction mixture is maintained at 75° C. for three to four hours. The product was cooled to 50° C. and the solvent was evaporated off at 70° C. in a vacuum oven overnight. The product was a liquid.

EXAMPLE 20

A 250 mL three-necked round bottom flask equipped with a mechanical stirrer, a thermometer, a water-cooled condenser, and a nitrogen gas inlet is charged with 62.67 grams (0.1485 mole) Ethomeen C-15 and 140 mL methylethyl ketone. The reaction mixture was stirred under a nitrogen blanket. Ethomeen C-15 in methylethyl ketone was then heated to 86° C. to azeotropically distill any water which was present in the solution. The solution was cooled to 50° C. and 0.25 grams isophorone diamine was charged. Then 20.18 grams (0.12 mole) 1,6-hexamethylene diisocyanate and 0.001 gram dibutyltin dilaurate were charged to the reaction vessel. The reaction mixture is maintained at 75° C. for three to four hours. The product was cooled to 50° C. and the solvent was evaporated off at 70° C. in a vacuum oven overnight. The product was a liquid.

The general procedure outlined in Example 20 was used, except that the reactants were replaced as indicated in Table 2. All examples were viscous liquids at ambient temperatures.

TABLE 2

| Example | Reagents | moles | wt. in grams. |
| --- | --- | --- | --- |
| 21 | Ethomeen C-15 | 0.1455 | 61.4 |
|  | Isophorone diamine | 0.005 | 0.7 |
|  | 1,6-Hexamethylene diisocyanate | 0.12 | 20.18 |

Evaluation of Rheological Additives

All the liquid materials prepared according to Examples 1–21 were incorporated by dispersing into a low VOC epoxy-polyamide two component system at a loading of 5 pounds per hundred gallons (pphg) and a number of tests were conducted to demonstrate the effectiveness of the respective rheological additive.

The preparation and components of a high solids polyester-melamine bake enamel paint is described in Formulation A. The ingredients were mixed using a Dispermat model CV, high speed dissolver fitted with a heavy duty 50 mm diameter impeller.

After the paints were made, they were allowed to equilibrate at room temperature overnight, and the paint properties were measured as described below:

(1) Fineness of grind (indicative of dispersibility) was measured in Hegman units using a wide path Hegman gauge in accordance with ASTM D1210-79.

(2) Brookfield viscosities at 10 and 100 RPM were measured with a Brookfield Model RVT viscometer in accordance with ASTM D2196-81. From viscosity data, a Thixotropic Index (TI) was calculated as follows:

Thixotropic Index (TI)=10 RPM Viscosity÷100 RPM Viscosity (3) Sag resistance was measured in mils using a Leneta Sag multi notch applicator at room temperature in accordance with ASTM D4400-84.

(4) In some instances Stormer viscosities were measured in Krebs Units (KU) with a Thomas Stormer Instrument, Model #09730-G15, in accordance with ASTM D562-81.

(5) Gloss measurements were measured at 60° and/or 20° in accordance with ASTM D523-80. Drawdowns were prepared of paints according to Formulation A, and the 60° and/or 20° gloss determined after curing the film for 24 hours at room temperature.

(6) Color values were measured on a Hunterlab Model D25-9 colorimeter in accordance with ASTM E-308.

Additionally, samples of rheological additives of the present invention were evaluated for Brookfield and Stormer viscosities, sag and gloss using the procedure discussed above in a low VOC epoxy-polyamide two component paint system at a loading of 5 pphg. The preparation and components of the low VOC epoxy-polyamide two component paint system are described in Formulation B, below.

The results of the tests are set forth in Table 4.

COMPARATIVE EXAMPLE 1

A high solids polyester bake enamel paint was prepared according to the procedure described in Formulation A without the addition of a rheological additive. The paint properties were evaluated and are set forth in Table 3.

Formulation A

High Solids Polyester-Melamine Bake Enamel Paint

| Material | Generic Name | Manufacturer | Wt. in grams |
|---|---|---|---|
| Polyester 57-5784 | High solids polyester resin | McWhorter Technologies | 407.3 |
| KRONOS 2090 | Titanium Dioxide | NL Industries, Inc. | 391.1 |
| Byk-300 | Slip aid | Byk-Chemie, USA. | 1 |
|  | Rheological additive |  | 9 |
| Propylene glycol monomethylether acetate | Solvent | ARCO | 19.6 |
| Disperse at 5,000 RPM for 15 minutes while maintaining the temperature @ 125° F. | | | |
| Melamine 2347 | Melamine resin | McWhorter Technologies | 122.2 |
| VP-451 | Amine salt of p-toluene sulfonic acid | Byk-Chemie, USA | 9.8 |
| Propylene glycol monomethylether acetate | Solvent | ARCO | 211.2 |
| Mix for 3 minutes at slow speed (2000 RPM) | | | |

TABLE 3

Results in High Solids Polyester Bake Enamel Paint
Loading: 9 pphg

| Example | Hegman Grind | Brookfield Viscosity, cP 10 RPM/100 RPM | TI | Leneta Sag (mil) | Stormer (KU) | Gloss 20°/60° |
|---|---|---|---|---|---|---|
| 1 | 7A | 3,250/672 | 4.84 | 20 | 67 | 88/71 |
| 3 | 7A | 1,280/360 | 3.56 | 7.9 | 61 | 92/80 |
| COMPARATIVE EXAMPLE 1 | 7A | 90/120 | 0.75 | 2 | 60 | 93/87 |

COMPARATIVE EXAMPLE 2

A low VOC epoxy-polyamide two component paint was prepared according to the procedures described in Formulation B without the addition of a rheological additive. The paint properties were evaluated and are set forth in Table 4.

Formulation B 0.6 (Lbs/Gal) VOC Epoxy-Polyamide Two Component Coating

| Material | Generic Name | Manufacturer | Wt. in grams |
|---|---|---|---|
| PART A | | | |
| Epon 828 | Epoxy Resin | SHELL CHEMICAL CO. | 343.8 |
| Silicon Resin | Silicon resin SR 882 solution | G.E. SILICON | 7 |
| Nuosperse 700 | Phosphate ester surfactant | HÜLS AMERCIA, INC. | 1 |
|  | Rheological Additive |  | 14.3 |
| Mix for 5 minutes at 3000 RPM, then add | | | |
| TITANOX 2101 | Titanium Dioxide | NL INDUSTRIES, INC. | 380 |
| Xylene | Solvent | ASHLAND CHEMICAL CO. | 26 |
| Disperse at 5,000 RPM for 15 minutes at 130° F., reduce speed to 1,500 RPM and add | | | |
| Epon 828 | Epoxy resin | SHELL CHEMICAL CO. | 115.2 |
| Mix at 1,500 RPM for 3 minutes and cool | | | |
| PART B | | | |
| Ancamide 506 | Amido Amine | PACIFIC ANCHOR CHEMICAL | 129 |
| Ancamide 1693 | Cycloaliphatic Amine | PACIFIC ANCHOR CHEMICAL | 129 |
| Toluene | Solvent | ASHLAND CHEMICAL CO. | 32 |
| Shake 10 minutes in a Red Devil Agitator. | | | |
| Mix 226 grams of Part A and 74 grams of Part B and shake for 3 minutes on a Red Devil Agitator. | | | |

TABLE 4

Results in a 0.6 (lbs/gal) VOC Epoxy-Polyamide two component system
Loading: 5 pphg

| | BASE PAINT | | CURED PAINT | | | | |
|---|---|---|---|---|---|---|---|
| Example | Brookfield Viscosity, cP 10 RPM/100 RPM | TI | Hegman Grind | Brookfield Viscosity, cP 10/100 RPM | TI | Stormer [KU] | Leneta Sag (mil) | Gloss 20°/60° |
| 1 | 90,000/33,000 | 2.73 | 6C | 8,120/2,900 | 2.8 | 114 | 25 | 91/99 |
| 2 | 90,000/35720 | 2.53 | 6C | 7,720/2,944 | 2.62 | 114 | 24 | 93/99 |
| 3 | 76,000/121,000 | 3.62 | 6C | 5,440/2,148 | 2.53 | 106 | 15 | — |
| 4 | 88,000/34,200 | 2.57 | 6C | 7,920/3,060 | 2.59 | 114 | 20 | 90/100 |
| 5 | 84,000/32,000 | 2.63 | 6C | 7,200/2,760 | 2.61 | 112 | 22 | 89/98 |
| 6 | 96,400/27,360 | 3.52 | 6C | 7,000/2,712 | 2.58 | 110 | 18 | — |

TABLE 4-continued

Results in a 0.6 (lbs/gal) VOC Epoxy-Polyamide two component system
Loading: 5 pphg

| Example | BASE PAINT Brookfield Viscosity, cP 10 RPM/100 RPM | TI | Hegman Grind | CURED PAINT Brookfield Viscosity, cP 10/100 RPM | TI | Stormer [KU] | Leneta Sag (mil) | Gloss 20°/60° |
|---|---|---|---|---|---|---|---|---|
| 7 | 92,000/25,600 | 3.59 | 5C | 6,000/2,340 | 2.56 | 108 | 16 | — |
| 8 | 69,200/26.100 | 2.65 | 6C | 8,000/3,000 | 2.67 | 113 | 24 | 90/98 |
| 9 | 66,800/25,600 | 2.61 | 3B | 6,800/2,720 | 2.50 | 113 | 17 | 89/98 |
| 10 | 69,000/19,600 | 3.52 | 6.5C | 5,120/2376 | 2.15 | 108 | 12 | 96/100 |
| 11 | 50,000/18,400 | 2.72 | 6.75B | 5,200/2,320 | 2.24 | 105 | 8 | 99/100 |
| 12 | 66,400/21,360 | 3.11 | 6.75A | 5,360/2,460 | 2.18 | 110 | 14 | 96/100 |
| 13 | 50,000/17,600 | 2.84 | 6.5A-B | 6,000/2,756 | 2.18 | 108 | 10 | 91/100 |
| 14 | 54,000/18,000 | 3.0 | 6.5A-B | 5,720/2,732 | 2.09 | 109 | 10 | 93/100 |
| 15 | 54,000/17,800 | 3.03 | 6.5C | 5,720/2,732 | 2.09 | 109 | 10 | 98/100 |
| 16 | 42,000/15,000 | 2.8 | 6.5B | 4,400/2,440 | 1.8 | 110 | 8 | 97/100 |
| 17 | 52,000/18,000 | 2.89 | 6.5B | 5,800/2,740 | 2.11 | 114 | 8 | 96/100 |
| 18 | 69,000/20,640 | 2.81 | 6.5C | 8,200/3,200 | 2.56 | 112 | 14 | — |
| 19 | 42,250/19,200 | 2.2 | 6.75 | 5,750/2,400 | 2.4 | 96 | 10 | 84/95 |
| 20 | 40,000/16,200 | 2.47 | 6.75B | 7,250/2,775 | 2.61 | 106 | 13 | 93/98 |
| 21 | 44,000/11,600 | 3.79 | 6.75 | 9,000/2,900 | 3.10 | 109 | 14 | 95/97 |
| COMPARATIVE EXAMPLE 2 | 4,000/4,000 | 1.00 | 7A | 1,040/1,016 | 1.03 | 96 | <3 | 98/99 |

Discussion of Results

As can be seen from the data set forth above, the liquid rheological additives described in Examples 1–9 are effective rheological additives yielding excellent viscosity results, antisag resistance and high thixotropic index in non-aqueous systems. As indicated in Table 4, the additives of Examples 10–21 result in lower but still useful antisag properties in epoxy-polyamide two component paint system. Therefore, it can be seen that the polymers represented by all the examples provide greater efficiencies in Brookfield and Stormer viscosities, TI and sag resistance in non-aqueous systems than comparative Example 2.

As can be seen from the data set forth above, the liquid rheological additives of the present invention are effective paint additives yielding excellent viscosity results compared to the several comparative examples in non-aqueous systems.

The invention being thus described, it will be obvious that the same may be varied in many ways and in a variety of obvious modifications. Such variations are not to be regarded as a departure from the spirit and scope of the invention as claimed below and are intended to be covered by its spirit.

What I claim:

1. A rheological additive for non-aqueous systems which when substantially free of diluent, is liquid and pourable at ambient temperatures, and imparts thixotropy to such systems, comprising the reaction product of:
   a) One or more active hydrogen compounds, wherein the active hydrogen compound contains at least two active hydrogen moieties selected from the group consisting of polyols, amino alcohols and diamines; and
   b) One or more polycarboxylic acids containing at least two reactive moieties which are capable of reacting with the active hydrogen moieties of (a);
wherein the active hydrogen moieties of compound a) are in stoichiometric excess of the reactive moieties of compound b) and the reaction product has at least two active hydrogen moieties at its termini.

2. The additive of claim 1 wherein one or more of the active hydrogen compounds of paragraph a) has the formula $(H-X)_m-R-(Y-H)_n$ where X and Y are independently selected from the group comprising heteroatoms, m and n are $\geq 1$ and R represents a group containing 2 to 100 carbon atoms.

3. The additive of claim 2 wherein the heteroatom is selected from the group consisting of oxygen and nitrogen.

4. The additive of claim 1 wherein the reaction product comprises:
   a) from about 15 to 95 parts by weight of compound a); and
   b) from about 5 to 85 parts by weight of compound b); wherein the active hydrogen moieties of compound a) are in stoichiometric excess of the reactive moieties of compound b) and the reaction product has at least two active hydrogen moieties in its termini.

5. The additive of claim 1 wherein the polyol is one or more polyether polyols.

6. The additive of claim 5 wherein the polyether polyol is selected from the group consisting of polyethylene glycols, polypropylene glycols, poly(ethylene-propylene) glycols, polybutylene oxides, and polytetrahydrofurans.

7. The additive of claim 1 wherein compound a) is selected from the group consisting of alkoxylated aliphatic amine diols and alkoxylated amide diols which are liquids at ambient temperatures.

8. The additive of claim 7 wherein one or more of the diols is selected from the group consisting of tertiary amines with one alkyl group.

9. The additive of claim 1 wherein compound a) is polyoxyethylene(5)cocoamine.

10. The additive of claim 1 wherein compound b) is a mixture of two or more different compounds.

11. A non-aqueous system containing the additive of claim 1.

12. The system of claim 11 wherein the system is selected from the group consisting of paints, coatings, inks, epoxies and polyesters.

13. The system of claim 11 wherein the system is paint.

14. A liquid rheological additive for non-aqueous systems pourable at ambient temperature which imparts thixotropy to such systems, comprising the reaction product of:

a) one or more compounds selected from the group consisting of polyols selected from the group consisting of 1,2 ethanediol, 1,2- and 1,3-propanediol 1,4- and 1,3-butanediol, 1,5-pentanediol, 1,6-hexanediol, 2-5-hexanediol and mixtures thereof, and diamines; and b) one or more compounds selected from the group consisting of polycarboxylic acids and polyisocyanates;

wherein the active hydrogen moieties of compound a) are in stoichiometric excess of the reactive moieties of compound b) and the reaction product has at least two active hydrogen moieties in its termini.

15. The additive of claim 14 wherein compound a) comprises from about 15 to 95 parts by weight of the reaction product.

16. The additive of claim 14 wherein compound a) is one or more alkoxylated aliphatic amine diols.

17. The additive of claim 16 wherein compound a) is one or more liquid alkoxylated aliphatic amine diols or alkoxylated aliphatic amide diols selected from tertiary amines with one or two alkyl groups having a general chemical structure represented by the following formula:

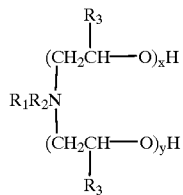

wherein:

(1) $R_1$ is a pendent straight or branched chain alkyl, saturated or unsaturated, radical having 6 to 40 carbon atoms, (2) $R_2$ is selected from the group comprising

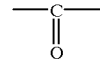

or —$CH_2$— and

3) $R_3$ is hydrogen or methyl.

18. The additive of claim 17 wherein $R_1$ has 10 to 18 carbon atoms.

19. The additive of claim 17 wherein $R_1$ is a fatty alkyl having 12 to 18 carbon atoms.

20. The additive of claim 13 wherein the fatty alkyl is selected from the group consisting of coco, stearyl, soya, tallow, hydrogenated tallow, oleyl and mixtures thereof.

21. The additive of claim 14 wherein the reaction product contains two active hydrogen moieties on its termini.

22. The additive of claim 14 dissolved in a diluent.

23. A non-aqueous system containing the additive of claim 14.

24. The system of claim 23 selected from the group consisting of paints, coatings, inks, epoxies and polyesters.

* * * * *